United States Patent
Chawla (10) Patent No.: US 7,025,057 B2
(45) Date of Patent: Apr. 11, 2006

(54) MEDICAMENT DELIVERY AND PACKAGING

(75) Inventor: Brindra Paul Singh Chawla, Nottingham (GB)

(73) Assignee: Technology Innovation Limited, Nottingham (GB)

( * ) Notice: Subject to any disclaimer, the term of this patent is extended or adjusted under 35 U.S.C. 154(b) by 0 days.

(21) Appl. No.: 10/506,909

(22) PCT Filed: Mar. 10, 2003

(86) PCT No.: PCT/GB03/01004

§ 371 (c)(1),
(2), (4) Date: Sep. 8, 2004

(87) PCT Pub. No.: WO03/075988

PCT Pub. Date: Sep. 18, 2003

(65) Prior Publication Data

US 2005/0115562 A1 Jun. 2, 2005

(30) Foreign Application Priority Data

Mar. 9, 2002 (GB) .................................. 0205572

(51) Int. Cl.
*A61M 15/00* (2006.01)

(52) U.S. Cl. ................................. 128/203.15

(58) Field of Classification Search ........... 128/203.15, 128/203.21, 203.23; 222/630–633
See application file for complete search history.

(56) References Cited

U.S. PATENT DOCUMENTS

| | | | |
|---|---|---|---|
| 4,860,740 A | 8/1989 | Kirk et al. | |
| 5,873,360 A | 2/1999 | Davies | |
| 6,418,926 B1 * | 7/2002 | Chawla | 128/203.12 |
| 6,520,179 B1 * | 2/2003 | Von Schuckmann et al. | 128/203.15 |

FOREIGN PATENT DOCUMENTS

| | | |
|---|---|---|
| EP | 0525 720 A1 | 2/1993 |
| EP | 1 172 122 A1 | 1/2002 |
| WO | PCT/GB97/03478 | 2/1998 |

* cited by examiner

*Primary Examiner*—Henry Bennett
*Assistant Examiner*—Shumaya B. Ali
(74) *Attorney, Agent, or Firm*—Woodling, Krost and Rust

(57) ABSTRACT

A system is disclosed for the administration of a powdered medicament by inhalation. The system comprises a container (20, 60, 120) containing a unit dose of medicament in powder form, the container (20, 60, 120) having at least one dispensing aperture (21), and a device (10, 50, 100) having a chamber (19, 56, 110) adapted to receive said container (20, 60, 120). The device (10, 50, 100) further comprises air inlet means (12, 12a, 13, 13a, 112, 113) by which air may be drawn into the chamber (19, 56, 110) and means (11, 111) by which air and entrained medicament may be drawn out of the chamber (19, 56, 110). The system is arranged such that the container (20, 60, 120), in use, is stationary within the chamber (19, 56, 110).

20 Claims, 5 Drawing Sheets

MEDICAMENT DELIVERY AND PACKAGING

This invention relates to delivery devices and packaging for medicaments, in particular to delivery devices and packaging for the administration of medicaments by inhalation.

The most common methods of administering powdered medicament by inhalation are pressurised aerosol inhalers and dry powder inhalers. Conventional dry powder inhalers use medicament packaged in a gelatine capsule. An improved method of administration, however, is disclosed in WO 98/26828.

WO 98/26828 discloses several delivery devices for use with medicament containers that contain pre-formed openings through which medicament is dispensed within the delivery device. The delivery devices all comprise a mouthpiece, air inlet means and a chamber in which the medicament container is located. In use, air is drawn into the chamber causing the medicament container to follow an orbital path around the chamber. In this way the medicament is dispensed through the openings of the medicament container and medicament entrained with air is drawn out of the chamber and through the mouthpiece. The disclosed delivery devices include single-use delivery devices pre-loaded with a medicament container and multi-use delivery devices in which a medicament container is inserted into the chamber before use.

The delivery devices and medicament packages disclosed in WO 98/26828 represent a considerable advance over the prior art, but are nonetheless susceptible to further improvement. In particular, the movement of the medicament container may, in use, be audible, which may be undesirable in certain situations.

There has now been devised an improved form of medicament delivery device and medicament packaging that overcomes or substantially mitigates the above-mentioned and/or other disadvantages of the prior art. In particular, it has surprisingly been found that a medicament container of the general type disclosed in WO 98/26828 may be caused to empty satisfactorily without undergoing movement.

According to the invention, there is provided a system for the administration of a powdered medicament by inhalation, the system comprising a container containing a unit dose of medicament in powder form, the container having at least one dispensing aperture, and a device having a chamber adapted to receive said container, the device further comprising air inlet means by which air may be drawn into the chamber and means by which air and entrained medicament may be drawn out of the chamber, wherein the system is arranged such that the container, in use, is stationary within the chamber.

The system according to the invention is advantageous primarily in that the medicament container empties without undergoing movement. As a result, the noise generated in use is low. Because the container does not need to undergo motion brought about by the airflow in the device, the required airflow in the device is relatively low, leading to greater ease of use, eg by users with impaired lung function.

It will be appreciated that inhalation of the medicament may be oral inhalation, or nasal inhalation. In either case, the device may be appropriately formed for the desired mode of administration. For example, the device may be formed with a mouthpiece or the like to facilitate inhalation. Likewise, for nasal inhalation, the device may be formed with an extension adapted to be offered up to, or inserted into, the user's nostril.

The device may be configured for single or repeated use. In either case, the device is preferably provided with means for storing the container, whilst sealing the at least one aperture, means for introducing the container into the chamber, and means for holding the container stationary within the chamber.

It will be appreciated that the system according to the invention may comprise a device and a single container, or a device and a plurality of containers. In the latter case, the plurality of containers may each contain the same medicament, or the containers may contain doses of two or more different medicaments, for simultaneous or sequential administration.

Where the system comprises a plurality of containers, those containers may be held in a magazine or cartridge that is coupled with the device to enable each container to be introduced sequentially into the chamber. For instance, the cartridge may take the form of a rotatable disk, suitable mechanical means being provided for indexing of the cartridge so as to bring the containers into registration with the chamber.

Preferably, the means for storing the container and introducing the container into the chamber take the form of an enclosure of deformable material arranged such that manual pressure introduces the container into the chamber.

According to another, more specific, aspect of the invention, there is provided a system for the administration of a powdered medicament by inhalation, the system comprising a container containing a unit dose of medicament in powder form, the container having at least one dispensing aperture, and a device having a chamber adapted to receive said container, the device further comprising air inlet means by which air may be drawn into the chamber and means by which air and entrained medicament may be drawn out of the chamber, wherein a part of the wall of the chamber is formed as a deformable enclosure within which the container is received such that the at least one dispensing aperture is sealed and from which the container can be introduced into the chamber by pressure applied to the external surface of the deformable enclosure, the system being arranged such that when the container is introduced into the chamber, the container is held stationary.

The container may be held stationary within the chamber by any suitable means. For instance, the container may be physically attached to the enclosure, such that when the enclosure is deformed and the container thereby introduced into the chamber the attachment of the container to the enclosure prevents movement of the container within the chamber. Alternatively, the container and/or the chamber may be provided with formations that are effective in holding the container in a stationary position once the container has been introduced into the chamber. For instance, the chamber may be provided with a recess in which the container is received when introduced into the chamber. Alternatively, the wall of the chamber that faces the enclosure may be provided with one or more projections that engage the container when the container is introduced into the chamber. In a further alternative, the container may be provided with one or more locating formations that engage with corresponding formations provided in the chamber. For instance, the container may be provided with a projecting lug that engages in a recess or opening formed in the wall of the chamber opposite to the enclosure. In a further alternative, there may be no physical attachment between the container and the chamber, but the dimensions of the container may be such that, when introduced into the chamber from the enclosure, it is simply captivated between opposing parts of the chamber, eg the base of the chamber and the periphery of the enclosure.

Where the container is physically attached to the enclosure, this may be by means of a projection formed on the container that extends through an opening in the enclosure. Such a projection may take the form of a stud, preferably formed integrally with the container, that projects through an opening in the enclosure and has an enlarged upper portion. Alternatively, the container may be bonded to the enclosure. Such bonding may be brought about by the application of heat and/or pressure, or alternatively by the use of adhesive.

In the case of a device intended for single use and then disposal, the means by which air and entrained medicament are drawn out of the chamber may simply comprise one or more apertures formed in a wall of the chamber. Preferably, these apertures and the air inlet means are sealed prior to use. Such a seal is most conveniently achieved by the provision of a removable sealing membrane, eg in the form of a laminated plastics sheet which is fixed in place by a suitable adhesive. The sealing membrane is preferably provided with a projecting portion or tab by which it can be grasped for ease of removal.

In the case of a device intended for repeated use, the enclosure and container may form a medicament package which may be attached to, and removed from, the delivery device. In such a case the medicament package preferably comprises a rigid support to which the enclosure is bonded, and the device is preferably provided with receiving means with which the rigid support can be engaged. Such receiving means may take the form of grooved formations with which the rigid support can be engaged. The receiving means are preferably provided adjacent an opening in the device such that engagement of the medicament package with the receiving means closes the opening.

The chamber is preferably circular in form. In some embodiments, the air inlet means are preferably arranged such that air enters the chamber substantially tangentially so as to facilitate the emptying of the container. There may be provided a plurality of air inlets, which may, but do not necessarily, open into the chamber at substantially equiangularly spaced positions.

The medicament container may have any shape. However, the container is preferably cylindrical or substantially cylindrical. In some embodiments, the diameter of the cylinder is typically comparable to or greater than its depth. For example, the depth of the cylinder may be no more than 1.5 times the diameter of the cylinder, and more preferably is equal to or less than the diameter. The container thus preferably has the form of a drum.

The medicament container is preferably provided with a plurality of dispensing apertures. In the case of a cylindrical container, the dispensing apertures are preferably disposed equiangularly around the cylindrical periphery of the container.

The device may be manufactured from materials conventionally utilised in inhalation drug delivery devices. For reasons of cost and manufacturing convenience, the device is most preferably manufactured by injection moulding in plastics material. Examples of suitable plastics materials include polycarbonate, polypropylene and polyethylene. Metals may also be used to form all or part of the device. Examples of suitable metals include aluminium and stainless steel. The device may be formed as a single injection-moulded component, or it may comprise a plurality of components that are subsequently bonded or otherwise connected together.

The enclosure is most preferably formed in deformable plastics material. The enclosure may be formed in the same material as the device, the necessary deformability being created if necessary by the use of material of reduced thickness. Alternatively, the enclosure may be formed in elastomeric material, most preferably a medical grade thermoplastic rubber. In such a case, the enclosure may be formed, together with the rest of the device (or the part of the device to which the enclosure is attached), or with the rigid support that together with the enclosure makes up a medicament package, by a two-shot moulding operation in which a first moulding is made in a relatively rigid plastics material and the elastomeric material is then moulded onto the first moulding.

The medicament container is preferably of a material which is substantially impermeable to moisture. The container is preferably of plastics material, most preferably polypropylene. The container may comprise two or more cooperating components that together define the container. Most preferably, the container is formed in two parts that fit together with a snap-fit or the like, one or both parts having formations that define the at least one dispensing aperture at the junction of the two parts. The two or more cooperating parts are preferably manufactured by injection moulding. As an alternative to the use of plastics materials, one or more parts of the container may be formed in metal, eg by pressing from a suitable sheet of metal. Metals that may be used include aluminium.

The invention will now be described in greater detail, by way of illustration only, with reference to the accompanying drawings, in which.

Figure 1:
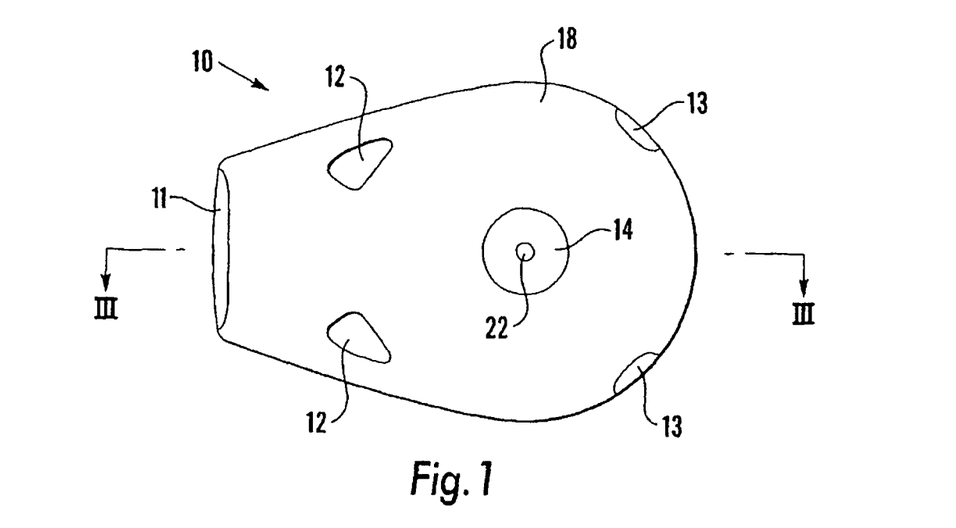
FIG. 1 is a plan view of a first embodiment of a powdered medicament inhaler according to the invention.
Figure 2:
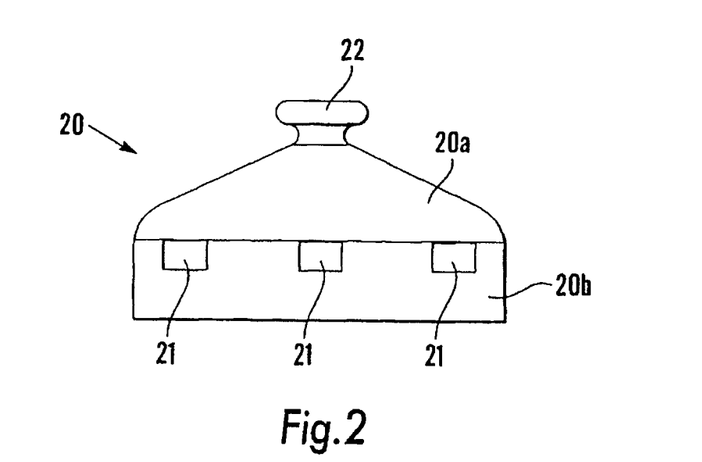
FIG. 2 is a side view of a medicament container that forms part of the inhaler of FIG. 1.

Referring first to FIGS. 1 and 2, a first embodiment of a medicament inhaler according to the invention is generally designated 10. The inhaler 10 comprises a main body 18, an enclosure 14 and a medicament container 20. The main body 18 and the medicament container 20 are both moulded in plastics material, whilst the enclosure 14 is of elastomeric material. In the drawings, the main body 18 is shown as a unitary component, but in practice it may be necessary or desirable for the main body 18 to be formed as two or more separate components that are assembled together in a subsequent fabrication step.

Referring to FIG. 2, the container 20 is formed from two interlocking components 20a and 20b, each of which is injection-moulded in plastics material, such that the container 20 has a cylindrical lower part and an upper part of generally domed or conical shape. The abutting edges of the two components 20a, 20b are formed so as to define a series of equiangularly spaced apertures 21. At the apex of the upper part of the container, the container 20 is formed with an integral stud 22 having an enlarged upper portion.

Figure 3:
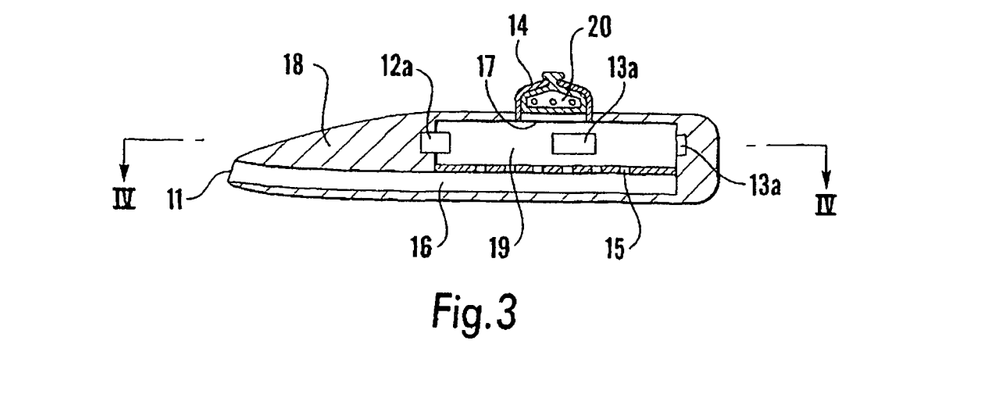
FIG. 3 is a sectional view along line III—III of FIG. 1.
Figure 4:
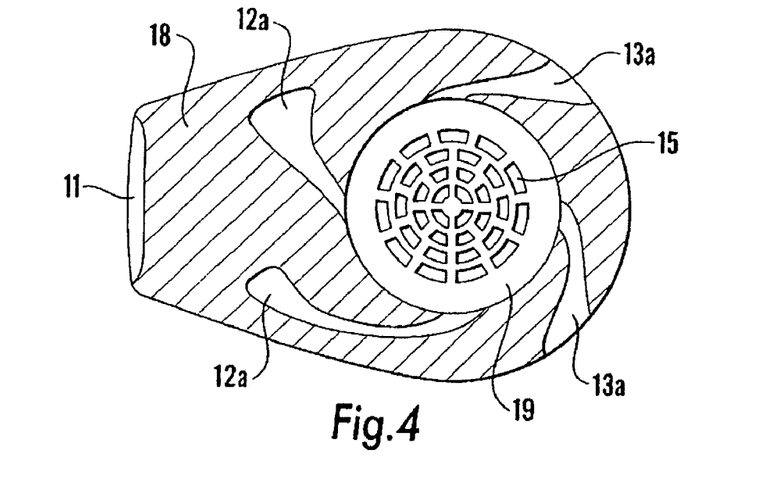
FIG. 4 is a sectional view along line IV—IV of FIG. 3.

Referring to FIGS. 1, 3 and 4, the main body 18 comprises a mouthpiece 11, a passageway 16, a chamber 19, conduits 12a, 13a and air inlets 12, 13. The mouthpiece is a generally elliptical opening in one end of the main body 18. The passageway extends from the mouthpiece 11 and through the lower part of the main body 18. The chamber 19 is cylindrical in shape and is positioned above the passageway 16. The chamber 19 communicates with the passageway 16 by means of a series of openings which make up a generally circular grid 15 in the centre of the base of the chamber 19, as shown in FIG. 4.

There are two front air inlets 12 and two rear air inlets 13 which connect the wall of the chamber 19 and the exterior of the inhaler 10 by means of respective conduits 12a, 13a, as shown in FIG. 4. The conduits 12a, 13a are aligned substantially tangentially to the wall of the chamber 19 and connect to the chamber 19 at equiangularly spaced locations.

Referring now to FIG. 3, the upper wall of the chamber 19 includes a circular aperture 17. The interior wall of the circular aperture 17 is bonded to the enclosure 14, the enclosure 14 extending above the chamber 19. The enclosure 14 is of similar shape to the container 20 save that the enclosure 14 has an open lower end and a circular aperture at its apex. The enclosure 14 is dimensioned such that the container 20 is closely received within the enclosure 14 with an interference fit and the stud 22 is pressed through the aperture of the enclosure 14, thereby holding the container 20 within the enclosure 14. The aperture of the enclosure 14 is dimensioned such that the lower portion of the stud fits closely within the aperture of the enclosure 14. The inhaler 10 is shown in FIG. 3 prior to use, with the medicament sealed within the container 10.

Figure 5:
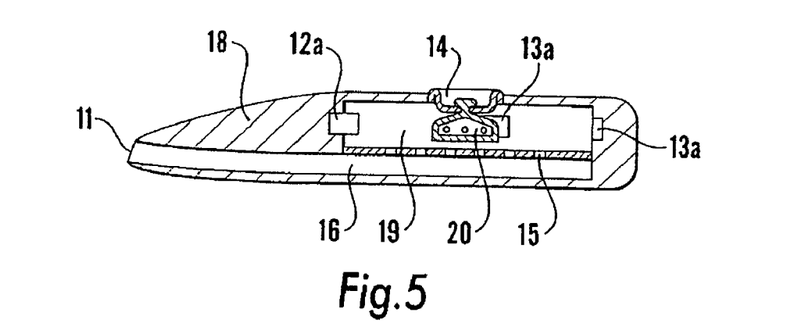
FIG. 5 is a sectional view, along line III—III of FIG. 1, of the inhaler in use.
Figure 6:
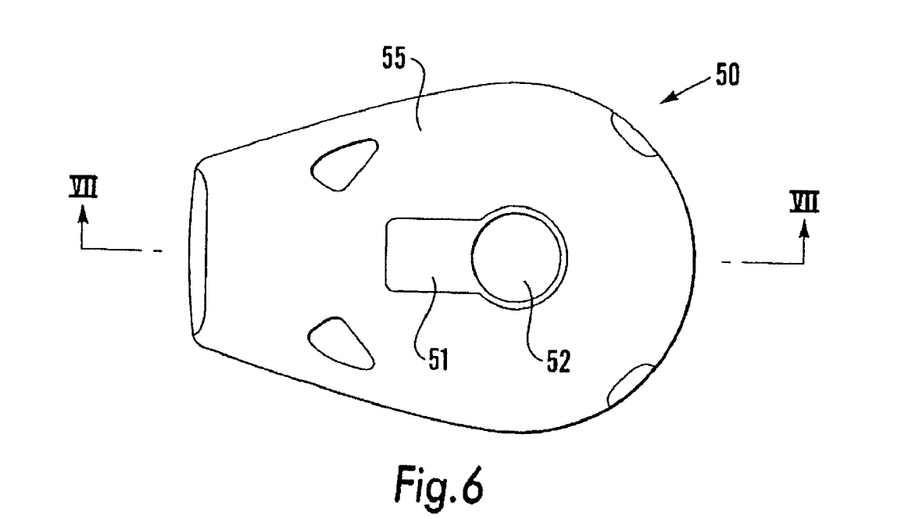
FIG. 6 is a plan view of a second embodiment of a powdered medicament inhaler according to the invention.

When the patient is ready to use the inhaler 10, the patient applies downward finger pressure on the enclosure 14 such that the enclosure 14 is turned inside out and extends partially into the chamber 19. The stud 22 projecting through the aperture of the enclosure 14 remains in this position thereby holding the container 20 in the centre of the chamber 19, as shown in FIG. 5.

The patient then places the mouthpiece 11 to their mouth and inhales. Air is drawn through the air inlets 12, 13, along the conduits 12a, 13a and substantially tangentially into the chamber 19. The airstream passes through the grid 15 and along the passageway 16 to the patients mouth. The stream of air entering the chamber 19 causes the medicament to be dispensed from within the medicament container 20, through the apertures 21 of the container 20, into the chamber 19. The medicament is entrained in the airstream which passes out of the chamber 19 through the grid and is inhaled by the patient. The first embodiment 10 is a single-use delivery device and would be discarded after use.

Turning now to FIGS. 6, 7, 8 and 9, a second embodiment of a medicament inhaler according to the invention is generally designated 50. The second embodiment 50 is similar to the first embodiment 10 save that the medicament container 61 and the enclosure 62 together form a separate component from the inhaler 50.

Figure 8:
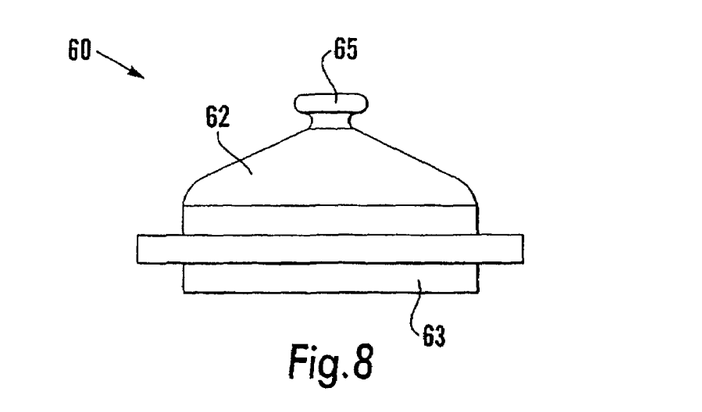
FIG. 8 is a side view of a medicament package according to the invention.
Figure 9:
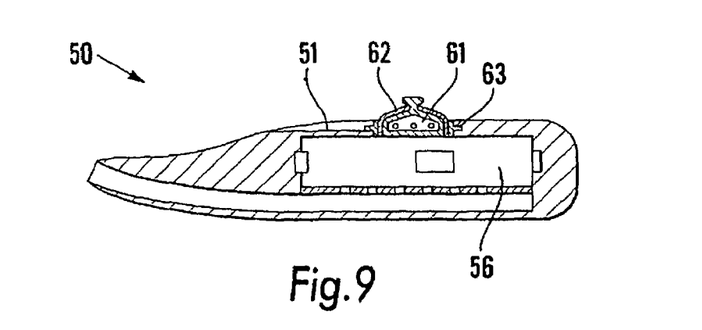
FIG. 9 is a view similar to that of FIG. 7, of the inhaler engaged with a medicament package.

The enclosure 62 and the medicament container 61, for use with the second embodiment of the inhaler 50, are identical to the enclosure 14 and container 20 of the first embodiment of inhaler 10. The enclosure 62 and container 61, together with a support ring 63, form a medicament package 60, as shown in FIG. 8. The container 61 is closely received with an interference fit, as in the first embodiment, within the enclosure 62, with the stud 65 of the container 61 projecting out of the aperture of the enclosure 62. The support ring 63 comprises an annular plate and a vertically orientated upper and lower skirt on the inner edge of the annular plate. The support ring 63 fits closely around, and is bonded to, the outside of the cylindrical lower section of the enclosure 62.

Figure 7:
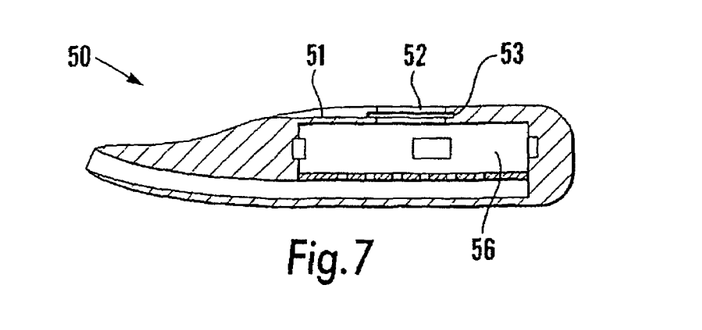
FIG. 7 is a sectional view along line VII—VII of FIG. 6.

The inhaler 50 is similar to the main body 18 of the first embodiment 10, save that the enclosure 62 is not bonded to the circular aperture 52 in the upper end of the chamber 56 The aperture 52 is provided with a peripheral groove 53 and an upper section of enlarged diameter, such that the support ring 63 of the medicament package 60 may be snap fitted from above into the groove 53 within the aperture 52. The upper surface of the inhaler 50 is provided with a rectangular depression 51 which extends from the aperture 52 and is dimensioned to accommodate the pad of the patient's thumb.

Figure 10:
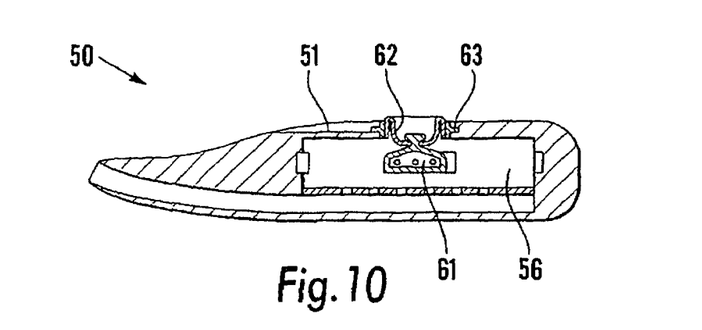
FIG. 10 is a view similar to that of FIG. 9, of the inhaler in use.

In order to load the inhaler 50, the medicament package 60 is snap-fitted, as described above, into the aperture 52, as shown in FIG. 10. The method of use is thenceforth identical to the method of use for the first embodiment 10. After use, however, the patient places their thumb in the depression 51 and exerts an upward pressure on the support ring 63 of the medicament package 60, thereby releasing the medicament package from the aperture 52. The inhaler 50 may subsequently be reloaded with another medicament package 60.

Figure 11:
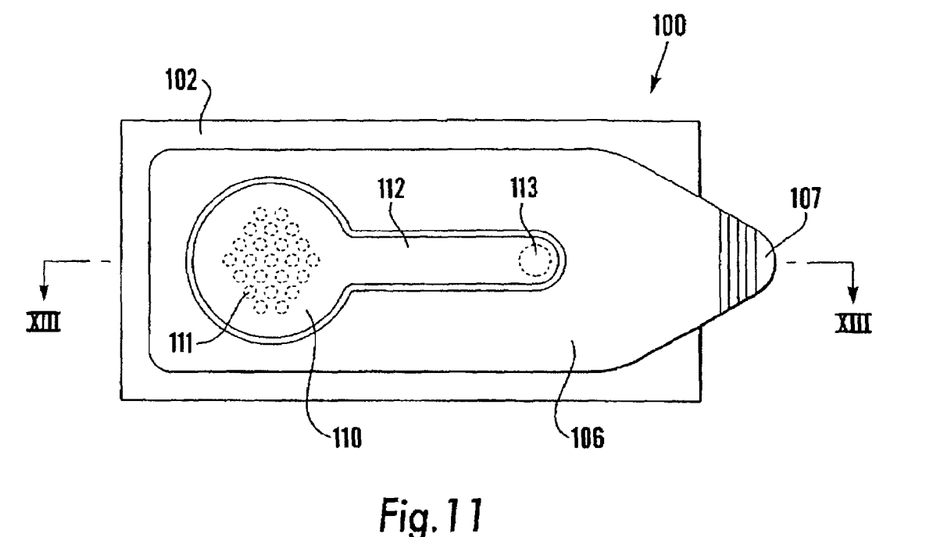
FIG. 11 is a front view of a third embodiment of a powdered medicament inhaler according to the invention.
Figure 12:
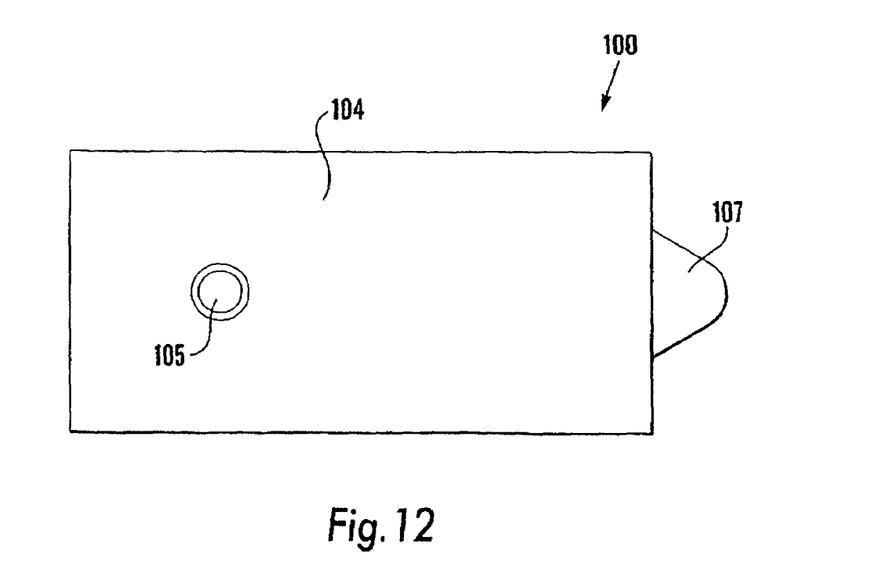
FIG. 12 is a rear view of the inhaler of FIG. 11.
Figure 13:
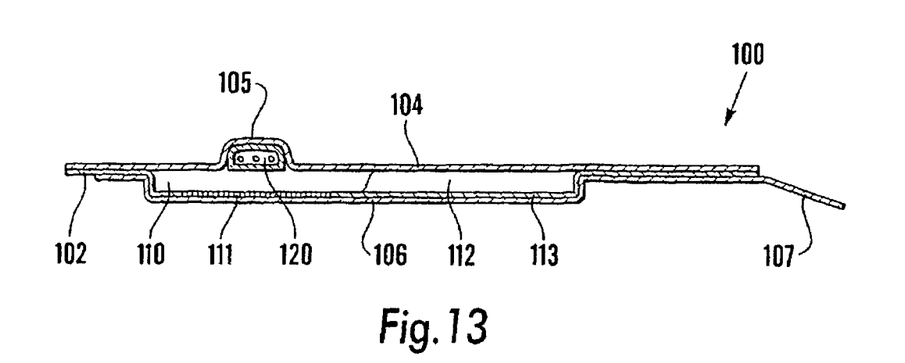
FIG. 13 is a sectional view along the line XIII—XIII of FIG. 11.

Turning now to FIGS. 11, 12 and 13, a third embodiment of a medicament inhaler according to the invention is generally designated 100. The inhaler 100 comprises a flat plastics rectangular base 104 heat-sealed to a formed plastics front portion 102, and a removable laminate cover sheet 106 glued to the outer surface of the front portion 102.

The front portion 102 defines a circular chamber 110 having a passageway 112 extending radially from the side wall of the chamber 110 along the longitudinal axis of the front portion 102. The passageway 112 has an air inlet 113 at the end of the passageway 112 remote from, but in fluid communication with, the chamber 110.

The base 104 includes a deformable enclosure 105 that accommodates a medicament container 120 with a close fit. The medicament container 120 contains a unit dose of medicament and is similar to the medicament containers 20 and 61 of the first and second embodiments save that medicament container 120 is generally cylindrical in form and does not have a stud corresponding to the studs 22,65 of the first and second embodiments. The deformable enclosure 105 is formed so as to seal apertures formed in the side of the container 120 and hold the container 120 in a position immediately adjacent the chamber 110.

The circular front wall of the chamber 110 includes an array of apertures 111. The front wall of the chamber 110 is adapted so as to be pressed to a patient's lips so that it may act as a mouthpiece. When cover sheet 106 is attached to the inhaler 100, prior to use, apertures 111 and air inlet 113 are sealed.

Figure 14:
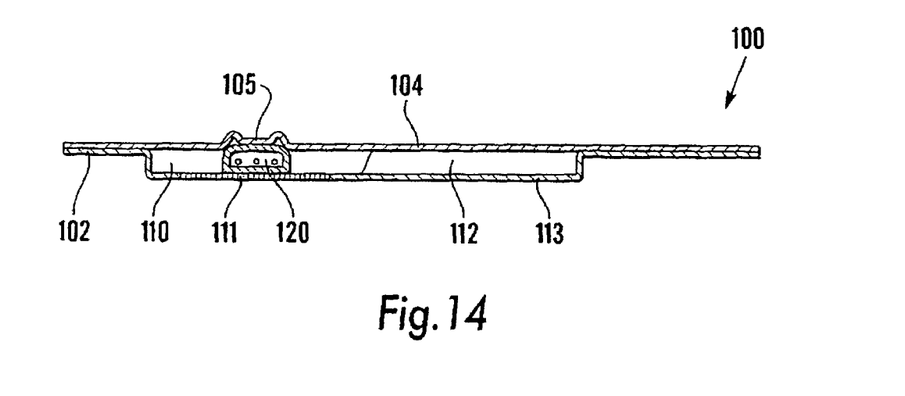
FIG. 14 is a view similar to that of FIG. 13 of the inhaler during use.

In order to use the inhaler 100, a patient simply pulls on a tab portion 107 of the cover sheet 106. The cover sheet 106 consequently peels away from the surface of the front portion 102 to open apertures 111 and air inlet 113. The deformable enclosure 105 is then depressed, and therefore deformed, using finger pressure so that the medicament container 120 is introduced into the chamber 110, as shown in FIG. 14. The depth of the chamber 110 is substantially the same as the depth of the container 120 and this, together with the resilience of the material from which the base 104 and front portion 102 are formed, results in the container 120 being held stationary within the chamber 110.

The mouthpiece is then offered up to the patient's lips, whereupon inhalation through the apertures 111 causes air to be drawn into air inlet 113, along passageway 112 and into chamber 110 where the unit dose of medicament contained within the medicament container 120 is entrained by the airstream and inhaled, through the apertures 111, by the patient.

Figure 15:
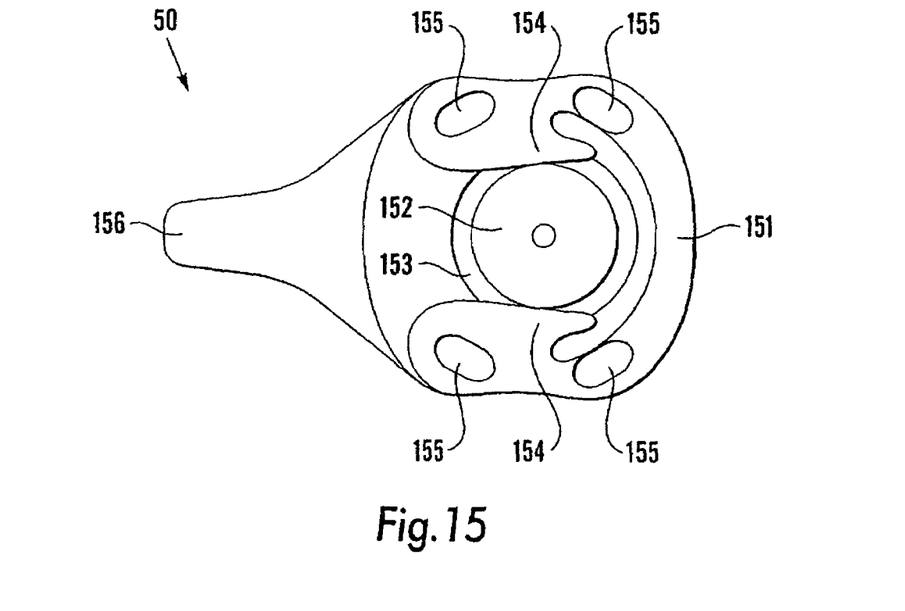
FIG. 15 is a plan view of a further embodiment of an inhaler according to the invention, adapted for nasal inhalation.

Finally, FIG. 15 shows a further embodiment of an inhaler 150 according to the invention. This embodiment 150 is broadly similar in function to that of FIGS. 6 and 7, in that it comprises a main body 151 with a removable medicament package comprising a flexible, dome-shaped enclosure 152 bonded to a rigid support ring 153. The ring 153 is slid beneath retaining formations 154 that are formed integrally with the main body 151 in order to position the enclosure 152 above the chamber of the device (not visible). Air inlets 155 communicate with the chamber in the same manner as for the previously-described embodiments. This embodiment differs from those previously-described embodiments in that the outlet 156 through which air, and entrained medicament, is withdrawn from the device is relatively narrow and is shaped and dimensioned for insertion into the user's nostril. This embodiment is therefore suitable for nasal inhalation.

The invention claimed is:

1. A system for the administration of a powdered medicamnent by inhalation, the system comprising a container containing a unit dose of medicatnent in powder form, the container having at least one dispensing aperture, and a device having a chamber adapted to receive said container, the device further comprising air inlet means by which air may be drawn into the chamber and means by which air and entrained medicament may be drawn out of the chamber, wherein a part of the wall of the chamber is formed as a deformable enclosure within which the container is received such that at least one dispensing aperture is sealed and from which the container can be introduced into the chamber by pressure applied to the external surface of the deformable enclosure, the system being arranged such that when the container is introduced into the chamber the container is held stationary.

2. A system as claimed in claim 1, wherein the system comprises a device and a plurality of medicament containers.

3. A system as claimed in claim 1, wherein the container is physically attached to the enclosure.

4. A system as claimed in claim 3, wherein the container is formed with a projection that extends through an opening in the enclosure.

5. A system as claimed in claim 3, wherein the container is bonded to the enclosure.

6. A system as claimed in claim 1, wherein the container and/or the chamber are provided with formations that are effective in holding the container in a stationary position once the container has been introduced into the chamber.

7. A system as claimed in claim 1, wherein the container is held stationary by virtue of being captivated between opposing parts of the chamber after being released from the enclosure.

8. A system as claimed in claim 1, wherein the means by which air and entrained medicament are withdrawn from the chamber comprises one or more apertures formed in a wall of the chamber.

9. A system as claimed in claim 8, wherein both the dispensing apertures and the air inlet means by which air is drawn into the chamber are sealed prior to use by a removable sealing membrane.

10. A system as claimed in claim 1, wherein the enclosure and container from a medicament package which may be removed from the delivery device.

11. A system as claimed in claim 10, wherein the medicament package comprises a rigid support to which the enclosure is bonded, and the device is provided with receiving means with which the rigid support can be engaged.

12. A system as claimed in claim 1, wherein the chamber is circular in form.

13. A system as claimed in claim 12, wherein the air inlet means are arranged such that air enters the chamber substantially tangentially so as to facilitate the emptying of the container.

14. A system as claimed in claim 1, wherein the device is provided with a plurality of air inlets opening into the chamber at substantially equiangularly spaced positions.

15. A system as claimed in claim 1, wherein the medicament container is cylindrical.

16. A system as claimed in claim 15, wherein the diameter of the cylinder is comparable to or greater than its depth.

17. A system as claimed in claim 16, wherein the depth of the cylinder is equal to or less than its diameter.

18. A system as claimed in claim 1, wherein the medicament container is provided with a plurality of dispensing apertures.

19. A system as claimed in claim 1, wherein the enclosure is of elastomeric material.

20. A system as claimed in claim 1, wherein the medicament container is of plastics material.

* * * * *

UNITED STATES PATENT AND TRADEMARK OFFICE
CERTIFICATE OF CORRECTION

PATENT NO. : 7,025,057 B2  Page 1 of 1
APPLICATION NO. : 10/506909
DATED : April 11, 2006
INVENTOR(S) : Brindra Paul Singh Chawla

It is certified that error appears in the above-identified patent and that said Letters Patent is hereby corrected as shown below:

Column 7, line 36, after "powdered" delete -medicamnent- and insert -- medicament--.

Column 7, line 38, after "of" delete -medicatnent- and insert -- medicament--.

Signed and Sealed this

Eleventh Day of July, 2006

JON W. DUDAS
*Director of the United States Patent and Trademark Office*